United States Patent [19]

Shewmaker

[11] Patent Number: 5,914,446
[45] Date of Patent: Jun. 22, 1999

[54] SOLUBLE SOLIDS MODIFICATION USING SUCROSE PHOSPHATE SYNTHASE ENCODING SEQUENCES

[75] Inventor: Christine K. Shewmaker, Woodland, Calif.

[73] Assignee: Calgene, LLC, Davis, Calif.

[21] Appl. No.: 08/549,016

[22] Filed: Oct. 27, 1995

Related U.S. Application Data

[63] Continuation-in-part of application No. 08/372,200, Jan. 12, 1995, Pat. No. 5,750,869.
[51] Int. Cl.$^6$ .............................. A01H 5/00; C12N 5/14; C12N 15/29; C12N 15/52; C12N 15/82
[52] U.S. Cl. ................... 800/205; 435/172.3; 435/320.1; 435/419; 536/23.2; 536/23.6; 800/DIG. 44
[58] Field of Search .............................. 435/172.3, 240.4, 435/320.1, 419; 800/205, DIG. 44; 536/23.2, 23.6

[56] References Cited

U.S. PATENT DOCUMENTS 5,536,653  7/1996  Barry et al. ........................... 435/172.3

FOREIGN PATENT DOCUMENTS

| | | |
|---|---|---|
| 0 438 904 | 7/1991 | United Kingdom . |
| 0 530 978 | 3/1993 | United Kingdom . |
| WO 92/14831 | 9/1992 | WIPO . |
| WO 92/16631 | 10/1992 | WIPO . |
| WO 93/06711 | 4/1993 | WIPO . |
| WO 93/14212 | 7/1993 | WIPO . |
| WO 94/00563 | 1/1994 | WIPO . |
| WO 94/28146 | 12/1994 | WIPO . |
| WO 96/21738 | 7/1996 | WIPO . |

OTHER PUBLICATIONS

Micallef et al. *Planta* (1995) 196:327–334.
Worrell et al., *The Plant Cell* (1991) 3: 1121–1130.
Klann et al., *Plant Physiology* (1992) 99: 351–353.
Galtier et al., *Plant Physiology* (1993) 101: 535–543.
Heineke et al., *Plant Physiology* (1992) 100: 301–308.
Lee et al., *Science* (1988) 239: 1288–1291.
Werr et al., *EMBO J.* (1985) 4: 1373–1380.
Preiss, *TIBS* (Jan., 1984) 24–27.
Micallef et al., *Planta* (1995) 196: 327–334.
Sonnewald et al., *Planta* (1993) 189: 174–181.
Klann et al., *Plant Physiology* (1993) 103: 863–870.
Kalt–Torres et al., *Physiol. Plantarum* (1987) 70: 653–658.
Kerr et al., *Planta* (1987) 170: 515–519.
Su et al., *Plant Physiol.* (1978) 61: 389–393.
Bruneau et al., *Plant Physiol.* (1991) 96: 473–478.
Kalt–Torres et al., (1987) Physiol. Plantarum vol. 70, pp. 653–658.
Dickinson et al. (Feb. 1991) Plant Physiol. vol. 95: pp. 420–425.
Von Schaewen et al. (1990) The EMBO Journal vol. 9 (10): pp. 3033–3044.
Sonnewald et al. (1993) Planta vol. 189: pp. 174–181.
Worrell et al. (1991) The Plant Cell vol. 3: pp. 1121–1130.
Institute fur Genbiologische Forschung Berlin GmbH "DNA Sequences and Plasmids for the Preparation of Plants with Changed Sucrose Concentration" Publication WO 94/00563 Published Jan. 6, 1994.
Hoechst Schering Agrevo GmbH "DNA Sequences and Plasmids for the Preparation of Sugar Beet with Changed Sucrose Concentration" Publication WO 94/28146 Published Dec. 8, 1994.
Zeneca Limited "Transgenic Plants with Increased Solids Content" Publication WO 93/14212 Published Jul. 22, 1993.
The Salk Institute Biotechnology/Industrial Associates "Novel Invertase Gene(s) and Uses Thereof" Publication WO 92/14831 Published Sep. 3, 1992.
The Regents of the University of California "Tomato Acid Invertase Gene" Publication WO 93/06711 Published Apr. 15, 1993.
Advanced Technologies Limited "Modification of Sucrose Accumulation" Publication EP 0 530 978 Published Mar. 10, 1993.
Advanced Technologies (Cambridge) Limited "Modification of plant metabolism" Publication No. EP 0 438 904 Published Jul. 31, 1991.
Roussel–Uclaf "Sucrose Phosphate Synthase (SPS), its Process for Preparation, its cDNA, and Utilization of cDNA to Modify the Expression of SPS in the Plant Cells" Publication No. WO 92/16631 Published Oct. 1, 1992.
Worrell, et. al., (1991) "Expression of a Maize Sucrose Phosphate Synthase in Tomato Alters Leaf Carbohydrate Partitioning" *The Plant Cell* 3 1121–1130.
Klann, et. al, "Tomato Fruit Acid Invertase Complementary DNA" *Plant Physiology* (1992) 99, 351–353.
Galtier, et. al, Effects of Elevated Sucrose–Phosphate Synthase Activity on Photosynthesis, Assimilate Partitioning and Growth in Tomato (*Lycopersicon Esculentum* var UC82B) *Plant Physiology* (1993) 101, 535–543.
Micallef, B.J., et al, "Altered photosynthesis, flowering, and fruiting in transgenic tomato plants that have an increased capacity for sucrose synthesis" *Biological Abstracts*, vol. 100, 1995 Philadelphia, PA, US; Abstract No. 42942.
Heineke, D., et al. "Apoplastic expression of yeast–derived inveertase in potato", *Plant Physiology*, vol. 100, 1992, pp. 301–308.

*Primary Examiner*—Douglas W. Robinson
*Assistant Examiner*—Amy J. Nelson
*Attorney, Agent, or Firm*—Rae-Venter Law Group, P.C.

[57] ABSTRACT

This invention relates to methods for the utilization of sucrose phosphate synthase encoding sequences to modify the soluble solids in plant sink tissue. The method permits an increase in the sweetness of tomato fruit.

13 Claims, No Drawings

SOLUBLE SOLIDS MODIFICATION USING SUCROSE PHOSPHATE SYNTHASE ENCODING SEQUENCES

RELATED APPLICATION DATA

The present application is a continuation-in-part of U.S. Pat. application Ser. No. 08/372,200, filed Jan. 12, 1995, now U.S. Pat. No 5,750,869.

TECHNICAL FIELD

The present invention is directed to compositions and methods related to modification of the sucrose biosynthesis pathway to alter the soluble solids content in selected plant tissue.

BACKGROUND

With the development of genetic engineering techniques, it is now possible to transfer genes from a variety of organism into the genome of a large number of different plant species. This process has many advantages over plant breeding techniques, as genes may now be transferred from one plant species to another plant species, rather than simply from a plant to the same, or different, but closely related, species.

Sucrose is one of the primary end products of photosynthesis in higher plants. It is also the major carbohydrate transported to sucrose accumulating, or carbon sink, tissues for plant growth and development (Pate, (1976) In: *Transport and Transfer Processes in Plants,* pp. 253–289, Wardlaw, J. F., Passioura, J. B., eds. Academic Press, N.Y.). Plant regions, such as leaf tissue, where sucrose is synthesized are commonly referred to as sucrose source tissue. Plant storage organs, such as roots or tubers, and fruits are examples of sink tissues.

Sucrose phosphate synthase (SPS) cDNA sequence, SPS constructs and transgenic SPS tomato lines are described in copending application, Ser. No. 08/175,471. This information is also published in Worrell et al. (*The Plant Cell* (1991) 3:1121–1130), incorporated herein by reference. In particular, the copending application describes a maize SPS under the control of the Rubisco small subunit promoter (SSU promoter) from tobacco, providing preferential expression in leaf tissue. Maximum activity of SPS is shown to be significantly increased in leaves of tomato plants expressing the maize SPS, and the absolute levels of starch and sucrose in the leaves are altered in the predicted manner.

Relevant Literature

SPS encoding sequences and the generation of transgenic tomato lines from the pCGN3812 SSU–SPS construct is described by Worrell et al. (*The Plant Cell* (1991) 3:1121–1130).

Galtier et al. (*Plant Physiol.* (1993) 101:535–543) examined the photosynthetic characteristics of SPS transformants.

In PCT Application WO 94/00563 antisense potato SPS is placed behind a tuber promoter and used to alter the sucrose levels in potato.

Acid invertase encoding sequences are described by Klann et. al., (*Plant Phys.* (1992) 99:351–353.)

SUMMARY OF THE INVENTION

By this invention, a method is disclosed whereby a construct encoding sucrose phosphate synthase (SPS) can be used to modify the solids content of plant sink tissue. Soluble solids include simple sugars, but also can include certain soluble polymers, and other soluble cell components. Total solids includes more complex carbon compounds, such as starches and cellulose. In one embodiment of the present invention, methods are disclosed for increasing the sweetness of fruit.

The method provided for increasing the total solids in a plant sink tissue will modify total solids from a given ratio of total solids per unit weight of sink tissue, as measured in control plant cells, to a different ratio of total solids per unit weight of sink tissue. The amount of sucrose available to growing tissues in the plant is increased, and the increased sucrose results in increased total solids per unit weight in the sink tissues of the plant. The method generally comprises growing a plant having integrated into its genome a construct comprising as operably linked components in the 5' to 3' direction of transcription, a transcription initiation region functional in a plant cell and a DNA encoding SPS.

The construct transcription initiation region may be constitutive or tissue specific, i.e., preferentially expressed and functional in cells of a particular plant tissue, for instance fruit or leaf. Many such tissue specific promoter regions are known, such as the Rubisco small subunit promoter preferentially expressed in leaf tissue, the patatin promoter expressed in potato tubers and the E8 promoter specific for fruit tissue.

In one embodiment the method produces sink tissue having increased carbon as soluble solids, as an increased ratio of soluble solids per unit weight of sink tissue, as compared to that measured in control plant cells. This results from the increased levels of sucrose generating an increased rate of transportation of the available sucrose into the carbon sink tissue.

In another embodiment a method is provided for modifying the soluble solids ratios in sink tissue, such as the ratio of sucrose to fructose, as compared to that measured in control plant cells or tissue. If the increased soluble solids in said sink tissue comprises fructose, a phenotype will result having an increased sweetness as opposed to the control tissue. Methods are also disclosed, however, whereby a decreased ratio of fructose to sucrose, and whereby a reduced sweetness phenotype may be produced.

The use of constructs comprising encoding sequences to other sucrose metabolizing enzymes, such as acid invertase, or the utilization of such enzymes which are endogenous to the plant sink cells, can be advantageously used with this invention. For instance, acid invertase can be expressed in the cells of sink tissue from an expression construct, or, alternatively, the sink tissue can be prevented from converting sucrose to fructose and glucose by the use of an antisense acid invertase construct, whereby cells of the sink tissue will have a decreased acid invertase activity, and thereby a decreased ratio of fructose to sucrose as compared to cells in a control sink tissue.

Considered part of this invention are the plants, plant cells and plant sink tissue transformed by nucleic acid sequences to SPS demonstrating a modified carbon solids content. The modification can be an increase in one or more solids components, or a change to the ratios of solids components.

In a particular embodiment, the invention provides fruit having increased total soluble solids and/or modified or increased fructose levels, as measured per unit weight.

A preferred embodiment includes fruit having a modified sweetness phenotype, either from a total increase in sweetness by percentage of fruit weight, or from an increased ratio of fructose to sucrose in the soluble solids.

Transformed plant cells of this invention are obtainable through plant transformation techniques which utilize Agrobacterium to transfer DNA to the plant cells or alternatively through direct transfer techniques such as electroporation, microinjection or DNA bombardment. In either case, plant carbon sink tissue, such as fruit, may be obtained which has increased or decreased soluble solids content and/or modified sweetness properties.

DETAILED DESCRIPTION OF THE INVENTION

This invention is directed to a method for producing plant cells demonstrating modified soluble solids content. The method utilizes a DNA sequence encoding SPS integrated in the cellular genome as the result of genetic engineering. Plant fruit which contains increased levels of soluble solids and an altered sweetness phenotype is also contemplated in this invention. The gene encoding SPS is described in copending application Ser. No. 08/175,471, filed on Dec.27, 1993.

The mechanism whereby the expression of exogenous SPS modifies carbon relationships derives from source-sink relationships. For instance, in those situations where SPS is expressed in leaves, plants have higher sugar and less starch in the leaves. The leaf tissue is a sucrose source, and if this higher sucrose is transported to a sink it results in increased storage carbon (sugars, starch, etc.) per given weight of the sink tissue.

The increased soluble solids in transgenic tomato lines transformed with SPS behind an SSU promoter showed an increase in glucose and fructose over sucrose. Similarly, when the fruit specific E8 promoter was used to express SPS, the resultant increase was in the form of the glucose and fructose.

By this invention, then, the increased carbon produced in a plant sink tissue in the form of soluble solids may be in the form of an increase in glucose and fructose levels as an alternative to, or as well as in, changes to levels of sucrose. In the tomato fruit glucose and fructose are produced from sucrose due to a vacuolar acid invertase that comes on during ripening. Acid invertase converts sucrose to glucose and fructose, and is known to affect fruit sweetness (Hubbard et al. (1991) *Physiol. Plant.* 82:191–196). It was not known prior to the invention whether an increase flow of sucrose into the fruit of tomato would be converted by exogenous acid invertase levels in this manner.

Fructose is twice as sweet, on a molar basis, as glucose, thus the invention provides a mechanism by which to selectively increase fructose in fruits for increasing sweetness. Thus, in one embodiment this invention produces tomato fruit (a sink tissue) having increased sweetness.

Thus, the method of altering sink tissue solids with sequences to SPS may be advantageously used in conjunction with endogenous sucrose metabolizing enzymes, whereby sequences to SPS are employed as the sole transformed encoding sequence. The method may also be employed in conjunction with other transformed sequences, for instance sequences encoding other sucrose metabolizing enzymes. Inhibition of certain sucrose metabolizing enzymes could result from the use of antisense expression. The inhibition of acid invertase in tomato fruit, for instance, can lead to fruit having elevated levels of sucrose in the tomato fruit. The sequence to acid invertase is known (Klann et al., (1992) *Plant. Phys.* (1992) 99:351–353). Expression of other sucrose metabolizing enzymes may result in alterations to other carbon components, for instance the expression of starch synthesizing enzymes to act in concert with the increased availability of sucrose may result in increased starch levels in the sink tissue. Such enzymes are known to the art, with many described in copending application having the Ser. No. 08/016,881, the teachings of which are incorporated herein by reference. The transformation of plants using glycogen synthesis enzymes (glgA, glgB and glgC) to modify starch compositions is described in U.S. Pat. No. 5,349,123.

A sucrose metabolizing enzyme considered in this invention includes any sequence of amino acids, such as protein, polypeptide, or peptide fragment, which demonstrates the ability to catalyze a reaction involved in the synthesis or degradation of sucrose or a precursor of sucrose. These can be endogenous plant sequences, by which is meant any sequence which can be naturally found in a plant cell, including native (indigenous) plant sequences as well as sequences from plant viruses or plant pathogenic bacteria, such as Agrobacterium or Rhizobium species that are naturally found and functional in plant cells.

It will be recognized by one of ordinary skill in the art that sucrose metabolizing enzyme sequences may also be modified using standard techniques of site specific mutation or PCR, or modification of the sequence may be accomplished in producing a synthetic nucleic acid sequence and will still be considered a sucrose biosynthesis enzyme nucleic acid sequence of this invention. For example, wobble positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of the instant invention.

A nucleic acid sequence to a sucrose metabolizing enzyme may be a DNA or RNA sequence, derived from genomic DNA, cDNA, mRNA, or may be synthesized in whole or in part. The structural gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene may be synthesized using codons preferred by a selected plant host. Plant-preferred codons may be determined, for example, from the codons used most frequently in the proteins expressed in a particular plant host species. Other modifications of the gene sequences may result in mutants having slightly altered activity. Once obtained, a sucrose metabolizing enzyme may be utilized with the SPS sequence in a variety of ways.

Other endogenous plant sequences may be useful in nucleic acid constructs of this invention, for example to provide for transcription of the sucrose metabolizing enzyme sequences. Transcriptional regulatory regions are located immediately 5' to the DNA sequences of the gene of interest, and may be obtained from sequences available in the literature, or identified and characterized by isolating genes having a desirable transcription pattern in plants, and studying the 5' nucleic acid sequences. Numerous transcription initiation regions which provide for a variety of constitutive or regulatable, e.g. inducible, expression in a plant cell are known. Among sequences known to be useful in providing for constitutive gene expression are regulatory regions associated with Agrobacterium genes, such as for nopaline synthase (Nos), mannopine synthase (Mas), or octopine synthase (Ocs), as well as regions coding for expression of viral genes, such as the 35S and 19S regions of cauliflower mosaic virus (CaMV). The term constitutive as used herein does not necessarily indicate that a gene is expressed at the same level in all cell types, but that the gene is expressed in a wide range of cell types, although some variation in abundance is often detectable.

In providing for transcription and/or expression of the sucrose metabolizing enzyme sequences, for various reasons one may wish to limit the expression of these enzymes to plant cells which function as carbon sinks. Towards this end, one can identify useful transcriptional initiation regions that provide for expression preferentially in specific tissue types, such as roots, tubers, seeds or fruit. These sequences may be identified from cDNA libraries using differential screening techniques, for example, or may be derived from sequences known in the literature. Useful transcriptional initiation regions preferentially provide for transcription in certain tissues or under certain growth conditions, such as those from napin, seed or leaf ACP, the small subunit of RUBISCO, patatin, zein, and the like. Fruit specific promoters are also known, one such promoter is the E8 promoter, described in Deikman et al. (1988) *EMBO J.* 2:3315–3320; and DellaPenna et al. (1989) *Plant Cell* 1:53–63, the teachings of which are incorporated herein by reference. An E8–SPS construct (fruit-specific promoter) will express SPS in a fruit-specific manner, whereby the levels of sucrose produced in the fruit may be elevated. If coupled with antisense invertase, the increase in sucrose would be maintained. This is a particular issue in tomatoes where acid invertase present in the fruit drives the production of glucose and fructose from sucrose.

Sequences to be transcribed are located 3' to the plant transcription initiation region and may be oriented, in the 5'–3' direction, in the sense orientation or the antisense orientation. In the sense orientation, an mRNA strand is produced which encodes the desired sucrose metabolizing enzyme, while in antisense constructs, an RNA sequence complementary to an enzyme coding sequence is produced. The sense orientation is desirable when one wishes to produce the sucrose metabolizing enzyme in plant cells, whereas the antisense strand may be useful to inhibit production of a related plant sucrose metabolizing enzymes. The presence of sucrose metabolizing enzyme sequences in the genome of the plant host cell may be confirmed, for example by a Southern analysis of DNA or a Northern analysis of RNA sequences or by PCR methods.

In addition to sequences providing for transcriptional initiation in a plant cell, also of interest are sequences which provide for transcriptional and translational initiation of a desired sequence encoding a sucrose metabolizing enzyme. Translational initiation regions may be provided from the source of the transcriptional initiation region or from the gene of interest. In this manner, expression of the sucrose metabolizing enzyme in a plant cell is provided. The presence of the sucrose metabolizing enzyme in the plant host cell may be confirmed by a variety of methods including an immunological analysis of the protein (e.g. Western or ELIZA), as a result of phenotypic changes observed in the cell, such as altered soluble solids content or by assay for increased enzyme activity, and the like.

Other sequences may be included in the nucleic acid construct providing for expression of the sucrose metabolizing enzymes ("expression constructs") of this invention, including endogenous plant transcription termination regions which will be located 3' to the desired sucrose metabolizing enzyme encoding sequence. For instance, transcription termination sequences derived from a patatin gene may be utilized when the sink tissue is potato tubers. Transcription termination regions may also be derived from genes other than those used to regulate the transcription in the nucleic acid constructs of this invention. Transcription termination regions may be derived from a variety of different gene sequences, including the Agrobacterium, viral and plant genes discussed above for their desirable 5' regulatory sequences.

Further constructs are considered which provide for transcription and/or expression of more than one sucrose metabolizing enzyme. For example, one may wish to provide enzymes to plant cells of the sink tissue which provide for modification of the type of soluble solids to be produced therein, as well as for enhancing or otherwise modifying the increase or decrease in overall soluble solids production. An example of enzymes which may prove useful in modifying soluble solids ratios is the acid invertase enzyme.

In developing the nucleic acid constructs of this invention, the various components of the construct or fragments thereof will normally be inserted into a convenient cloning vector, e.g. a plasmid, which is capable of replication in a bacterial host, e.g. *E. coli*. Numerous vectors exist that have been described in the literature, many of which are commercially available. After each cloning, the cloning vector with the desired insert may be isolated and subjected to further manipulation, such as restriction, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

The constructs of this invention providing for transcription and/or expression of sucrose metabolizing enzyme sequences of this invention may be utilized as vectors for plant cell transformation. The manner in which nucleic acid sequences are introduced into the plant host cell is not critical to this invention. Direct DNA transfer techniques, such as electroporation, microinjection or DNA bombardment may be useful. To aid in identification of transformed plant cells, the constructs of this invention may be further manipulated to include plant selectable markers. The use of plant selectable markers is preferred in this invention as the amount of experimentation required to detect plant cells is greatly reduced when a selectable marker is expressed. Useful selectable markers include enzymes which provide for resistance to an antibiotic such as gentamycin, hygromycin, kanamycin, and the like. Similarly, enzymes providing for production of a compound identifiable by color change, such as GUS, or luminescence, such as luciferase are useful.

An alternative method of plant cell transformation employs plant vectors which contain additional sequences which provide for transfer of the desired sucrose metabolizing enzyme sequences to a plant host cell and stable integration of these sequences into the genome of the desired plant host. Selectable markers may also be useful in these nucleic acid constructs to provide for differentiation of plant cells containing the desired sequences from those which have only the native genetic material. Sequences useful in providing for transfer of nucleic acid sequences to host plant cells may be derived from plant pathogenic bacteria, such as Agrobacterium or Rhizogenes, plant pathogenic viruses, or plant transposable elements.

When Agrobacterium is utilized for plant transformation, it may be desirable to have the desired nucleic acid sequences bordered on one or both ends by T-DNA, in particular the left and right border regions, and more particularly, at least the right border region. These border regions may also be useful when other methods of transformation are employed.

Where Agrobacterium or Rhizogenes sequences are utilized for plant transformation, a vector may be used which may be introduced into an Agrobacterium host for homologous recombination with the T-DNA on the Ti- or Ri-plasmid present in the host. The Ti- or Ri- containing the T-DNA for recombination may be armed (capable of causing gall formation), or disarmed (incapable of causing gall formation), the latter being permissible so long as a functional complement of the vir genes, which encode trans-acting factors necessary for transfer of DNA to plant host cells, is present in the transformed Agrobacterium host. Using an armed Agrobacterium strain can result in a mixture of normal plant cells, some of which contain the desired nucleic acid sequences, and plant cells capable of gall formation due to the presence of tumor formation genes. Cells containing the desired nucleic acid sequences, but lacking tumor genes can be selected from the mixture such that normal transgenic plants may be obtained.

In a preferred method where Agrobacterium is used as the vehicle for transforming host plant cells, the expression or transcription construct bordered by the T-DNA border region (s) will be inserted into a broad host range vector capable of replication in $E.$ $coli$ and Agrobacterium, there being broad host range vectors described in the literature. Commonly used is pRK2 or derivatives thereof. See, for example, Ditta, et al., ($Proc.$ $Nat.$ $Acad.$ $Sci.,$ $U.S.A.$ (1980) 77:7347–7351) and EPA 0 120 515, which are incorporated herein by reference. Alternatively, one may insert the sequences to be expressed in plant cells into a vector containing separate replication sequences, one of which stabilizes the vector in $E.$ $coli,$ and the other in Agrobacterium. See, for example, McBride and Summerfelt ($Plant$ $Mol.$ $Biol.$ (1990) 14:269–276), wherein the pRiHRI (Jouanin, et al., $Mol.$ $Gen.$ $Genet.$ (1985) 201:370–374) origin of replication is utilized and provides for added stability of the plant expression vectors in host Agrobacterium cells.

Utilizing vectors such as those described above, which can replicate in Agrobacterium is preferred. In this manner, recombination of plasmids is not required and the host Agrobacterium vir regions can supply trans-acting factors required for transfer of the T-DNA bordered sequences to plant host cells.

In general, the plant vectors of this invention will contain sucrose metabolizing enzyme sequence(s) and sequences providing for transcription or expression of these sequences in a plant host cell. The plant vectors containing the desired sequences may be employed with a wide variety of plant cells and plants. Fruit producing plants and plants which produce and store reserve starch are of particular interest, the latter including, but in no way limited to, corn, cereal grains, sorghum, rice, potato, tapioca, cassava, arrowroot and sago. The method may also be useful in increasing the sweetness in fruits, including, but in no way limited to, tomato, strawberry and melon.

Also considered part of this invention are plants containing the nucleic acid sequences of this invention, and following from that, plants modified by the expression of SPS and possibly additional sucrose metabolizing enzymes as the result of expression of the sequences in plant cells, or having a decreased expression of a such by the inhibition of such additional sucrose metabolizing enzymes from antisense expression of the encoding sequences. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations either from seed or using vegetative propagation techniques.

The invention now being generally described, it will be more readily understood by reference to the following examples which are included for purposes of illustration only and are not intended to limit the present invention.

Measurement of specific gravity or free sugar content may be useful to detect modified sweetness or total soluble solids, with other methods, such as HPLC and gel filtration, also being useful.

EXAMPLES

Constructs and plants with the designations 3812 and 3815 are as described in copending application Ser. No. 08/175,471, which in turn is a continuation of U.S. Pat. application Ser. No. 07/672,646, both of which are incorporated by reference. Briefly, the construct pCGN3812 contains the construct 5'-35S-nptII-tm1-3'/5'= tobacco Rubisco SSU-maize SPS cDNA-3'. The construct pCGN3815 contains the construct 5'-35S-nptII-tm1-3'/ 5'35S–maize SPS cDNA–3'. Tomato lines arising from separate transformation events are signified by a hyphen and a number following the construct designation.

Example 1

Soluble Solids in T2 SSU–SPS Plants

Investigation of the soluble solids in the fruits of the SSU-SPS lines was initially done on extracts from fruit of 3812-9 and 3812-11 lines grown in a Biotron incubator. T2 plants were illuminated by metal halide lamps at a peak level of 500 $\mu$mol photons/m/s (pot level), 26 C for the 16 h day and 18 C at night, and a relative humidity of 60% Plants were watered daily with half-strength Hoagland's solution (Hoagland and Arnon, $Calif.$ $Agricult.$ $Exp.$ $Sta.$ $Cir.$ (1938) 357:1–39). These lines were segregating as the original lines contained at least 2 insertions.

Brix analysis (soluble solids) on extracts from these plants revealed lines with Brix readings as much as 40% higher than the controls. The extracts measured were the average of 3 fruit from one plant.

Measurements were also taken for fruit from a segregating T2 population of 3812-11 plants in the greenhouse. The controls averaged a Brix reading of 3.5 while the transgenics averaged 4.0, an increase of 14%.

Example 2

Homozygous Plants

T4 homozygous lines were generated from original 3812-9 transformants in UC82-B tomatoes. The original line segregated 15:1 for Kan resistance, indicating that is it had two insertion sites. Two homozygous lines were generated and verified to be different by Southern border analysis. These lines were designated A and B.

Individual homozygote (T4) lines were grown in the greenhouse, with three fruit taken from each plant and 3 plants analyzed from each line. The Brix of the UC82B controls was 3.35 while the Brix on the 3812-9 lines ranged from 3.7 to 4.1. This is an increase from 12% to 24%. Statistics (LSD) on all the lines in which fruit from 3 plants were analyzed showed these results to be significant at a 0.01% level (99%).

Measurements were also made on homozygous lines of tomato plants transformed with the 35S CaMV promoter-SPS construct pCGN3815. In one line, 3815-13-2 there was a substantial increase in yield of tomatoes, in terms of an increase in both fruit size and in fruit number, as measured against non-transformed control plants and as against SSU-SPS homozygous line controls. The 3815-13-2 plants also produced a second flush of fruit. A second transgenic line containing the pCGN3815 construct did not produce these dramatic yield increases.

Example 3

Brix Analysis of Field Trial SSU-SPS Fruit

Field trial results of RI measurements are provided in Table 1. The R/I (refractive index) was measured several times on the fruit of these plants (Table 1). R/I is a measure of soluble solids and is indicative of sugars and acids. The transgenic A lines consistently had a higher R/I (3.9 to 4.1) than the control. (3.5).

TABLE 1

Summary of Refractive Index Measurements

| Line | Reading I | Reading 2 | Reading 3 | Reading 4 | Overall Aug |
|---|---|---|---|---|---|
| Trial 1 | | | | | |
| UC82-B | 3.3 | 3.9 | 3.6 | 3.0 | 3.5 |
| A Lines (X2) | 4.0 | 4.4 | 4.6 | 3.8 | 4.2 |
| Trial 2 | | | | | |
| UC82-B | 4.1 | 4.1 | 3.9 | | 4.0 |
| A Lines (X3) | 4.8 | 4.3 | 4.2 | | 4.4 |
| B Lines (X2) | 4.4 | 4.4 | 4.2 | | 4.3 |
| Trial 3 | | | | | |
| UC82B | 3.2 | | | | |
| A Lines (X1) | 4.2 | | | | |
| B Lines (X1) | 4.2 | | | | |

TABLE 2

Sugars of Tomatoes of plants transformed with SPS Gene

| ID # | Tomato line | RI | Sucrose | Glucose | Fructose | Total | Relative increase over control |
|---|---|---|---|---|---|---|---|
| 41000 #1 | Control | 3.9 | 0.08 | 1.33 | 1.62 | 3.03 | |
| 41000 #2 | Control | 4.2 | 0.11 | 1.51 | 1.75 | 3.37 | |
| 41003 | SSU-SPS-A-75-5 | 4.9 | 0.19 | 1.58 | 2.58 | 4.35 | 36% |
| 41004 | SSU-SPS-A-91-4 | 4.9 | 0.19 | 1.61 | 2.55 | 4.35 | 36% |
| 41008 | SSU-SPS-B-87-2 | 4.6 | 0.22 | 1.59 | 2.37 | 4.18 | 31% |
| Average increase due to SPS | | 0.18 | 0.10 | 0.17 | 0.81 | 1.09 | 34% |

Example 4

HPLC Analysis on SSU-SPS Fruit Sugars

Fruit from the SPS plants described in Example 3 were further analyzed by HPLC to determine contributions of individual sugars to the increased soluble solids content. As seen in Table 2, sucrose did not increase as much as might be expected based on the fact that sucrose is the sugar transported by the plant into the fruit. Glucose was not increased as much as fructose, which increased nearly 50%.

It is evident from the above results, that plant cells and plants can be produced which have improved properties or may produce a desired phenotype. In accordance with the subject invention, it is now seen that SPS sequences may be introduced into a plant host cell and be used to express the enzyme to increase soluble solids content in fruit. Moreover, it is seen that the SPS may be used to alter the overall content and ratio of soluble solids in plant sink tissue, resulting in a demonstrable phenotype in planta, such as altered fruit sweetness. In this manner, fruits, such as tomato fruit, having modified sweetness may be obtained.

Example 5

Fruit Specific Expression of SPS

E8-SPS constructs designated as pCGN3342 and pCGN3343 contain the tomato E8 promoter comprising the approximately 2.1 kb 5' region of the E8 promoter. A description of this promoter region can be found in Deikman et al., supra, and in Deikman et al. (*Plant Physiol.* (1992) 100:2013–2017).

This E8 promoter is fused to the same SPS encoding sequence used for pCGN3812 and pCGN3815, only the SPS sequence used in these constructs has been truncated at the ApoI site just 3' of the SPS encoding sequence (at nucleotide 3318), and fused to a 1.2 kb region of the tml 3' region from pTiA6 (Barker et al., (1983) Plant Mol. Biol. 2:335–350; sequence 11207–10069 of the T-DNA region from the *Agrobacterium tumefaciens* Ti plasmid pTi15955). Constructs pCGN3342 and pCGN3343 are the opposite orientations of this E8-SPS-tml construct in the 35S kan binary, pCGN1557 (McBride and Summerfelt, supra). Tomato lines arising from separate transformation events using pCGN3342 and pCGN3343 are signified by the construct number followed by a hyphen and an event number.

Table 3 provides data from RI measurements of soluble solids in tomatoes from greenhouse studies of T1 plants. The R/I (refractive index) was measured several times on the fruit of these plants.

TABLE 3

| | Date | RI of transgenic | RI of control |
|---|---|---|---|
| 3343-6 | 4/11/95 | 7.2 | 6.0 |
| | 4/28/95 | 8.2 | 5.2 |
| | 5/30/95 | 10.2 | 7.5 |
| 3342-11 | 3/29/95 | 7.9 | 4.9 |
| | 4/4/95 | 7.6 | 6.2 |

TABLE 3-continued

| | Date | RI of transgenic | RI of control |
|---|---|---|---|
| | | | (4/7/95) |
| 3343-22 | 5/10/95 | 7.8 | 6.8 |
| | | | (5/12/95) |
| | 5/12/95 | 8.5 | 6.8 |
| | 5/16/95 | 7.6 | 7.0 |
| | 5/19/95 | 8.2 | 6.6 |
| 3343-56 | 5/23/95 | 7.6 | 6.1 |
| | 5/30/95 | 8.0 | 7.5 |
| | 5/31/95 | 9.1 | 6.0 |

Assays were made for the SPS activity in control and transgenic fruit from the 3343–6 and 3342–11 events. The control 7060 fruit was assayed with a SPS activity rate of 17.8 μmols sucrose/gram fresh weight/hour. Activity was much higher in the transgenic lines, with the 3343-6 event having a rate of 67.5 μmols sucrose/g/hr and 3342-11 event measured at 36.6 μmols sucrose/g/hr. This demonstrates that the increase sugar concentration of fruit in transgenic tomatoes over the control correlates to an increase of SPS activity in the fruit.

Tables 4 and 5 provide an analysis of individual sugars as measured by HPLC from two separate trials, to determine contributions of each sugar to the increased soluble solids content observed in transgenic E8-SPS fruit. The data of table 4 and 5 demonstrate that increased SPS activity from transgenic expression in fruit by a fruit specific promoter can produce an overall net increase in sugars in the fruit. Due to the endogenous acid invertase found in ripening tomato fruit, increases in sugar are found in glucose and fructose.

TABLE 4

Sugars of SPS Tomato Lines

| | | | Sugar content (%) | | | |
|---|---|---|---|---|---|---|
| Line ID | Date | RI | Sucrose | Glucose | Fructose | Total |
| Control | 3/29/95 | 4.4 | 0.00 | 2.30 | 1.49 | 3.79 |
| 3342-11 | 3/29/95 | 7.9 | 0.00 | 3.64 | 3.29 | 6.93 |
| 3342-11 | 3/31/95 | 6.1 | 0.00 | 3.02 | 2.48 | 5.50 |
| 3342-11 | 4/4/95 | 7.5 | 0.00 | 3.12 | 3.27 | 6.39 |
| 3342-14 | 3/29/95 | 7.2 | 0.00 | 3.54 | 3.21 | 6.75 |
| 3342-14 | 4/4/95 | 8.4 | 0.00 | 4.13 | 3.72 | 7.85 |
| 3342-23 | 3/29/95 | 8.5 | 0.52* | 3.34 | 3.37 | 7.23 |
| 3343-5 | 4/4/95 | 4.0 | 0.00 | 1.66 | 1.27 | 2.93 |
| 3812-6 | 4/4/95 | 8.5 | 0.00 | 3.95 | 3.57 | 7.52 |

It also appears that there is a correlating increase in acid levels with an increase in sugar content in fruit transformed with E8-SPS.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

What is claimed is:

1. A method of increasing the sweetness of fruit in a transgenic plant, as compared to that measured in tissue of fruit of control plants not comprising an exogenous sucrose phosphate synthase gene, said method comprising:

growing a plant having integrated into its genome a first construct comprising, as operably linked components in the 5' to 3' direction of transcription, a fruit specific transcription initiation region and a DNA sequence encoding sucrose phosphate synthase, and wherein said plant is grown under conditions which permit said fruit specific transcription initiation region to function, whereby sweetness of said fruit is increased.

2. The method of claim 1 wherein cells of said fruit have an increased level of sucrose as compared to that of a cell in a control fruit.

3. The method of claim 1 wherein cells of said fruit have an increased level of fructose as compared to that to that of a cell in a control fruit.

4. The method of claim 1 wherein cells of said fruit have an increased level of glucose as compared to that to that of a cell in a control fruit.

5. The method of claim 1 wherein said fruit specific transcription initiation region is from the E8 promoter.

6. The method of claim 1 wherein said plant is a tomato.

7. The method according to claim 1 wherein said DNA sequence encoding sucrose phosphate is from maize.

8. The method of claim 1, wherein said fruit has endogenous acid invertase activity.

9. A method of increasing the sweetness of tomato fruit, said method comprising:

growing a tomato plant having integrated into its genome a construct, said construst comprising, as operably linked components in the 5' to 3' direction of transcription, a CaMV 35S promoter or a tobaccco

TABLE 5

Sugars and Acids of SPS Tomato Lines

| Line ID | Date | RI | Sucrose | Glucose | Fructose | G/F | Total Sugars | Titratable Acidity |
|---|---|---|---|---|---|---|---|---|
| 7060 | 5/19/95 | 6.6 | N.D. | 3.10 | 2.78 | 1.12 | 5.88 | 0.384 |
| 3343-22 | 5/19/95 | 8.2 | N.D. | 4.40 | 3.79 | 1.16 | 8.18 | 0.608 |
| 3342-16 | 5/19/95 | 8.2 | N.D. | 4.23 | 3.71 | 1.14 | 7.94 | 0.555 |
| FL7060 | 5/31/95 | 6.2 | N.D. | 3.01 | 2.36 | 1.28 | 5.37 | 0.448 |
| 3343-56 | 5/31/95 | 8.1 | N.D. | 4.64 | 4.08 | 1.14 | 8.72 | — |
| 3812-29 | 5/31/95 | 9.5 | N.D. | 5.13 | 4.21 | 1.22 | 9.33 | — |
| 3343-6 | 5/30/95 | 10.4 | .36 | 4.91 | 4.69 | 1.05 | 9.97 | .0597 |
| 3343-6 | 5/2/95 | 8.2 | N.D. | 3.95 | 3.68 | 1.07 | 7.63 | .0640 |
| FL7060 | 5/2/95 | 4.9 | N.D. | 2.33 | 1.79 | 1.30 | 4.11 | 0.432 |
| FL7060 | 5/12/95 | 6.8 | N.D. | 3.46 | 2.84 | 1.21 | 6.29 | 0.533 |
| 3343-22 | 5/12/95 | 8.5 | N.D. | 4.24 | 3.57 | 1.19 | 7.81 | — |

Rubisco small subunit promoter, and a maize-derived DNA sequence encoding sucrose phosphate synthase, wherein said plant is grown under conditions which permit said transcription initiation region to function in said fruit of said plant, whereby sweetness of said fruit is increased as compared to that measured in tissue of fruit of control plants not comprising an exogenous sucrose phosphate synthase gene.

10. A plant fruit cell having increased sugar content produced according to the method of claim 1.

11. A tomato fruit cell according to claim 10.

12. A plant comprising a cell according to claim 10.

13. A tomato plant according to claim 12.

* * * * *